(12) United States Patent
Willyard et al.

(10) Patent No.: US 10,022,186 B2
(45) Date of Patent: *Jul. 17, 2018

(54) MICROWAVE ANTENNA WITH COOLED HANDLE

(71) Applicant: COVIDIEN LP, Mansfield, MA (US)

(72) Inventors: Richard A. Willyard, Loveland, CO (US); Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/642,071

(22) Filed: Jul. 5, 2017

(65) Prior Publication Data

US 2017/0312030 A1    Nov. 2, 2017

Related U.S. Application Data

(63) Continuation of application No. 15/194,810, filed on Jun. 28, 2016, now Pat. No. 9,707,038, which is a (Continued)

(51) Int. Cl.
*A61B 18/00* (2006.01)
*A61B 18/18* (2006.01)
(Continued)

(52) U.S. Cl.
CPC .......... *A61B 18/1815* (2013.01); *A61B 18/18* (2013.01); *H01Q 1/02* (2013.01);
(Continued)

(58) Field of Classification Search
CPC .............. A61B 18/18; A61B 18/1815; A61B 2018/00011; A61B 2018/00017;
(Continued)

(56) References Cited

U.S. PATENT DOCUMENTS 3,631,363 A    12/1971   Miller
D223,367 S    4/1972   Kountz
(Continued)

FOREIGN PATENT DOCUMENTS

CN    1103807 C    3/2003
DE    390937 C    3/1924
(Continued)

OTHER PUBLICATIONS

US 5,326,343, 07/1994, Rudie et al. (withdrawn)
(Continued)

*Primary Examiner* — Michael Carey

(57) ABSTRACT

According to one aspect of the present disclosure, a microwave antenna assembly is disclosed. The antenna assembly includes a feedline having an inner conductor, an outer conductor and an inner insulator disposed therebetween and a radiating portion including a dipole antenna having a proximal portion and a distal portion. The antenna assembly also comprises a sheath disposed over the feedline and the radiating portion defining a chamber around the feedline and the radiating portion. The chamber is adapted to circulate coolant fluid therethrough. The antenna assembly further includes a connection hub having cable connector coupled to the feedline, an inlet fluid port and an outlet fluid port. The connection hub includes a bypass tube configured to provide for flow of the coolant fluid from the cable connector directly to the outlet fluid port.

20 Claims, 10 Drawing Sheets

Related U.S. Application Data continuation of application No. 14/925,025, filed on Oct. 28, 2015, now Pat. No. 9,375,280, which is a continuation of application No. 14/659,860, filed on Mar. 17, 2015, now Pat. No. 9,198,725, which is a continuation of application No. 14/338,509, filed on Jul. 23, 2014, now Pat. No. 9,113,932, which is a continuation of application No. 14/014,937, filed on Aug. 30, 2013, now Pat. No. 8,795,268, which is a continuation of application No. 13/596,785, filed on Aug. 28, 2012, now Pat. No. 8,523,854, which is a continuation of application No. 12/199,935, filed on Aug. 28, 2008, now Pat. No. 8,251,987.

(51) Int. Cl.
*H01Q 9/16* (2006.01)
*H01Q 1/02* (2006.01)

(52) U.S. Cl.
CPC ...... *H01Q 9/16* (2013.01); *A61B 2018/00011* (2013.01); *A61B 2018/00017* (2013.01); *A61B 2018/00023* (2013.01); *A61B 2018/00577* (2013.01); *A61B 2018/1838* (2013.01); *A61B 2018/1861* (2013.01); *A61B 2018/1869* (2013.01); *A61B 2018/1892* (2013.01); *Y10T 29/49016* (2015.01)

(58) Field of Classification Search
CPC .......... A61B 2018/00023; A61B 2018/00577; A61B 2018/1838; A61B 2018/1861; A61B 2018/1869; A61B 2018/1892; H01Q 1/02; H01Q 9/16; Y10T 29/49016
USPC ..................................................... 606/32, 33
See application file for complete search history.

(56) References Cited

U.S. PATENT DOCUMENTS

| | | |
|---|---|---|
| 3,693,613 A | 9/1972 | Kelman |
| 4,140,130 A | 2/1979 | Storm, III |
| D263,020 S | 2/1982 | Rau, III |
| D266,842 S | 11/1982 | Villers et al. |
| 4,375,220 A | 3/1983 | Matvias |
| 4,397,313 A | 8/1983 | Vaguine |
| 4,462,412 A | 7/1984 | Turner |
| D278,306 S | 4/1985 | McIntosh |
| 4,572,190 A | 2/1986 | Azam et al. |
| 4,658,836 A | 4/1987 | Turner |
| 4,662,383 A | 5/1987 | Sogawa et al. |
| D295,893 S | 5/1988 | Sharkany et al. |
| D295,894 S | 5/1988 | Sharkany et al. |
| 4,798,215 A | 1/1989 | Turner |
| 4,823,812 A | 4/1989 | Eshel et al. |
| 5,097,844 A | 3/1992 | Turner |
| 5,234,004 A | 8/1993 | Hascoet et al. |
| 5,344,435 A | 9/1994 | Turner et al. |
| 5,370,676 A | 12/1994 | Sozanski et al. |
| D354,218 S | 1/1995 | Van de Peer |
| 5,411,520 A | 5/1995 | Nash et al. |
| 5,413,588 A | 5/1995 | Rudie et al. |
| 5,417,210 A | 5/1995 | Funda et al. |
| 5,417,686 A | 5/1995 | Peterson et al. |
| 5,421,829 A | 6/1995 | Olichney et al. |
| 5,464,445 A | 11/1995 | Rudie et al. |
| 5,480,417 A | 1/1996 | Hascoet et al. |
| 5,509,929 A | 4/1996 | Hascoet et al. |
| 5,535,818 A | 7/1996 | Fujisaki et al. |
| 5,545,137 A | 8/1996 | Rudie et al. |
| 5,599,295 A | 2/1997 | Rosen et al. |
| 5,628,770 A | 5/1997 | Thome et al. |
| 5,755,754 A | 5/1998 | Rudie et al. |
| 5,775,338 A | 7/1998 | Hastings |
| 5,776,176 A | 7/1998 | Rudie |
| 5,800,486 A | 9/1998 | Thome et al. |
| 5,829,519 A | 11/1998 | Uthe |
| 5,843,144 A | 12/1998 | Rudie et al. |
| 5,861,021 A | 1/1999 | Thome et al. |
| 5,904,709 A | 5/1999 | Amdt et al. |
| 5,916,240 A | 6/1999 | Rudie et al. |
| 5,916,241 A | 6/1999 | Rudie et al. |
| 5,931,860 A | 8/1999 | Reid et al. |
| 5,938,692 A | 8/1999 | Rudie |
| 5,944,749 A | 8/1999 | Fenn |
| 5,951,546 A | 9/1999 | Lorentzen |
| 6,007,571 A | 12/1999 | Neilson et al. |
| 6,031,375 A | 2/2000 | Atalar et al. |
| 6,032,078 A | 2/2000 | Rudie |
| D424,693 S | 5/2000 | Pruter |
| D424,694 S | 5/2000 | Tetzlaff et al. |
| D425,201 S | 5/2000 | Tetzlaff et al. |
| 6,059,780 A | 5/2000 | Gough et al. |
| 6,097,985 A | 8/2000 | Kasevich et al. |
| 6,134,476 A | 10/2000 | Arndt et al. |
| 6,161,049 A | 12/2000 | Rudie et al. |
| 6,181,970 B1 | 1/2001 | Kasevich |
| 6,230,060 B1 | 5/2001 | Mawhinney |
| 6,233,490 B1 | 5/2001 | Kasevich |
| 6,275,738 B1 | 8/2001 | Kasevich et al. |
| 6,289,249 B1 | 9/2001 | Amdt et al. |
| D449,886 S | 10/2001 | Tetzlaff et al. |
| 6,364,876 B1 | 4/2002 | Erb et al. |
| 6,375,606 B1 | 4/2002 | Garibaldi et al. |
| D457,958 S | 5/2002 | Dycus et al. |
| D457,959 S | 5/2002 | Tetzlaff et al. |
| 6,383,180 B1 | 5/2002 | Lalonde et al. |
| 6,440,158 B1 | 8/2002 | Saab |
| 6,451,015 B1 | 9/2002 | Rittman, III et al. |
| 6,470,217 B1 | 10/2002 | Fenn et al. |
| 6,496,737 B2 | 12/2002 | Rudie et al. |
| 6,512,956 B2 | 1/2003 | Amdt et al. |
| 6,592,577 B2 | 7/2003 | Abboud et al. |
| 6,592,579 B2 | 7/2003 | Amdt et al. |
| 6,603,994 B2 | 8/2003 | Wallace et al. |
| 6,610,054 B1 | 8/2003 | Edwards et al. |
| 6,635,053 B1 | 10/2003 | Lalonde et al. |
| 6,675,050 B2 | 1/2004 | Arndt et al. |
| 6,682,525 B2 | 1/2004 | Lalonde et al. |
| D487,039 S | 2/2004 | Webster et al. |
| 6,725,080 B2 | 4/2004 | Melkent et al. |
| 6,725,095 B2 | 4/2004 | Fenn et al. |
| D496,997 S | 10/2004 | Dycus et al. |
| D499,181 S | 11/2004 | Dycus et al. |
| 6,847,848 B2 | 1/2005 | Sterzer et al. |
| 6,849,063 B1 | 2/2005 | Eshel et al. |
| 6,866,624 B2 | 3/2005 | Chornenky et al. |
| 6,944,504 B1 | 9/2005 | Arndt et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| 7,244,254 B2 | 7/2007 | Brace et al. |
| 7,271,363 B2 | 9/2007 | Lee et al. |
| 7,276,061 B2 | 10/2007 | Schaer et al. |
| 7,303,554 B2 | 12/2007 | Lalonde et al. |
| 7,311,703 B2 | 12/2007 | Turovskiy et al. |
| D564,662 S | 3/2008 | Moses et al. |
| 7,387,627 B2 | 6/2008 | Erb et al. |
| D576,932 S | 9/2008 | Strehler |
| 7,439,736 B2 | 10/2008 | Meaney et al. |
| 7,467,015 B2 | 12/2008 | van der Weide |
| D594,736 S | 6/2009 | Esjunin |
| D594,737 S | 6/2009 | Kelly et al. |
| 7,565,207 B2 | 7/2009 | Turner et al. |
| D606,203 S | 12/2009 | Husheer et al. |
| 7,642,451 B2 | 1/2010 | Bonn |
| D613,412 S | 4/2010 | DeCarlo |
| 7,875,024 B2 | 1/2011 | Turovskiy et al. |
| D634,010 S | 3/2011 | DeCarlo |
| 8,035,570 B2 | 10/2011 | Prakash et al. |

(56) References Cited

U.S. PATENT DOCUMENTS

| | | | |
|---|---|---|---|
| 8,059,059 B2 | 11/2011 | Bonn | |
| 8,118,808 B2 | 2/2012 | Smith et al. | |
| 8,182,480 B2 | 5/2012 | Huseman | |
| 8,192,427 B2 | 6/2012 | Buysse | |
| 8,197,473 B2 | 6/2012 | Rossetto et al. | |
| 8,202,270 B2 | 6/2012 | Rossetto et al. | |
| 8,211,098 B2 | 7/2012 | Paulus | |
| 8,211,099 B2 | 7/2012 | Buysse et al. | |
| 8,216,227 B2 | 7/2012 | Podhajsky | |
| 8,221,418 B2 | 7/2012 | Prakash et al. | |
| 8,235,981 B2 | 8/2012 | Prakash et al. | |
| 8,246,614 B2 | 8/2012 | DeCarlo | |
| 8,251,987 B2* | 8/2012 | Willyard | A61B 18/18 606/33 |
| 8,262,703 B2 | 9/2012 | Prakash et al. | |
| 8,292,880 B2 | 10/2012 | Prakash et al. | |
| 8,292,881 B2 | 10/2012 | Brannan et al. | |
| 8,343,149 B2 | 1/2013 | Rossetto et al. | |
| 8,353,902 B2 | 1/2013 | Prakash | |
| 8,353,903 B2 | 1/2013 | Podhajsky | |
| 8,394,086 B2 | 3/2013 | Behnke et al. | |
| 8,435,237 B2 | 5/2013 | Bahney | |
| 8,463,396 B2 | 6/2013 | Podhajsky | |
| 8,480,666 B2 | 7/2013 | Buysse et al. | |
| 8,486,057 B2 | 7/2013 | Behnke, II | |
| 8,512,328 B2 | 8/2013 | Rossetto et al. | |
| 8,512,329 B2 | 8/2013 | Paulus | |
| 8,523,854 B2* | 9/2013 | Willyard | A61B 18/18 606/33 |
| 8,568,402 B2 | 10/2013 | Buysse et al. | |
| 8,608,731 B2 | 12/2013 | Rossetto et al. | |
| 8,667,674 B2 | 3/2014 | Buysse | |
| 8,668,688 B2 | 3/2014 | Rusin | |
| 8,679,108 B2 | 3/2014 | Rossetto et al. | |
| 8,690,869 B2 | 4/2014 | Prakash et al. | |
| 8,745,846 B2 | 6/2014 | Behnke, II et al. | |
| 8,795,268 B2* | 8/2014 | Willyard | A61B 18/18 606/32 |
| 8,801,709 B2 | 8/2014 | Prakash et al. | |
| 8,834,409 B2 | 9/2014 | Manley | |
| 8,834,460 B2 | 9/2014 | Peterson | |
| 8,870,860 B2 | 10/2014 | Lee et al. | |
| 8,906,008 B2 | 12/2014 | Brannan et al. | |
| 8,920,410 B2 | 12/2014 | Brannan | |
| 8,945,111 B2 | 2/2015 | Brannan et al. | |
| 8,945,113 B2 | 2/2015 | Brannan et al. | |
| 8,965,536 B2 | 2/2015 | Bonn et al. | |
| 8,968,290 B2 | 3/2015 | Brannan et al. | |
| 8,969,722 B2 | 3/2015 | Bonn | |
| 8,992,413 B2 | 3/2015 | Bonn et al. | |
| 9,023,025 B2 | 5/2015 | Behnke, II et al. | |
| 9,033,970 B2 | 5/2015 | Behnke, II et al. | |
| 9,039,692 B2 | 5/2015 | Behnke, II et al. | |
| 9,039,693 B2 | 5/2015 | Behnke, II et al. | |
| 9,113,924 B2 | 8/2015 | Brannan et al. | |
| 9,113,930 B2 | 8/2015 | Reid, Jr. | |
| 9,113,931 B2 | 8/2015 | Lee et al. | |
| 9,113,932 B1* | 8/2015 | Willyard | A61B 18/18 |
| 9,119,648 B2 | 9/2015 | Lee et al. | |
| 9,168,178 B2 | 10/2015 | Reid, Jr. et al. | |
| 9,173,706 B2 | 11/2015 | Rossetto | |
| 9,192,308 B2 | 11/2015 | Brannan et al. | |
| 9,198,723 B2 | 12/2015 | Paulus et al. | |
| 9,198,724 B2 | 12/2015 | Brannan | |
| 9,198,725 B2* | 12/2015 | Willyard | A61B 18/18 |
| 9,271,796 B2 | 3/2016 | Buysse et al. | |
| 9,277,969 B2 | 3/2016 | Brannan et al. | |
| 9,364,278 B2 | 6/2016 | DeCarlo et al. | |
| 9,375,272 B2 | 6/2016 | Rossetto et al. | |
| 9,375,274 B2 | 6/2016 | Reid, Jr. | |
| 9,375,280 B2* | 6/2016 | Willyard | A61B 18/18 |
| 9,579,150 B2 | 2/2017 | DeCarlo | |
| 9,700,366 B2 | 7/2017 | Paulus | |
| 9,707,038 B2* | 7/2017 | Willyard | A61B 18/18 |
| 2002/0022836 A1 | 2/2002 | Goble et al. | |
| 2003/0032951 A1 | 2/2003 | Rittman et al. | |
| 2004/0097805 A1 | 5/2004 | Verard et al. | |
| 2004/0133254 A1 | 7/2004 | Sterzer et al. | |
| 2004/0242992 A1 | 12/2004 | Hareyama | |
| 2005/0015081 A1* | 1/2005 | Turovskiy | A61B 18/18 606/33 |
| 2005/0113893 A1 | 5/2005 | Saab | |
| 2005/0149010 A1 | 7/2005 | Turovskiy et al. | |
| 2005/0245920 A1 | 11/2005 | Vitullo et al. | |
| 2006/0259024 A1 | 11/2006 | Turovskiy et al. | |
| 2006/0293650 A1* | 12/2006 | Prakash | A61B 18/18 606/33 |
| 2007/0016180 A1 | 1/2007 | Lee et al. | |
| 2007/0016181 A1 | 1/2007 | van der Weide et al. | |
| 2007/0203551 A1 | 8/2007 | Cronin et al. | |
| 2008/0308256 A1 | 12/2008 | Deborski et al. | |
| 2009/0248005 A1 | 10/2009 | Rusin et al. | |
| 2010/0030206 A1 | 2/2010 | Brannan et al. | |
| 2010/0045559 A1 | 2/2010 | Rossetto | |
| 2010/0076422 A1 | 3/2010 | Podhajsky | |
| 2010/0087808 A1 | 4/2010 | Paulus | |
| 2010/0262134 A1 | 10/2010 | Jensen et al. | |
| 2011/0060326 A1 | 3/2011 | Smith et al. | |
| 2011/0238053 A1 | 9/2011 | Brannan et al. | |
| 2012/0239024 A1 | 9/2012 | Ladtkow et al. | |
| 2012/0239030 A1 | 9/2012 | Ladtkow | |
| 2012/0253341 A1 | 10/2012 | Paulus | |
| 2012/0303018 A1 | 11/2012 | Ladtkow et al. | |
| 2013/0218143 A1 | 8/2013 | Ross | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1238263 B | 4/1967 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3711511 C1 | 6/1988 |
| DE | 3712328 A1 | 10/1988 |
| DE | 3904558 A1 | 8/1990 |
| DE | 3942998 A1 | 7/1991 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 246350 A1 | 11/1987 |
| EP | 0481685 A1 | 4/1992 |
| EP | 0521264 A2 | 1/1993 |
| EP | 556705 A1 | 8/1993 |

(56) References Cited

FOREIGN PATENT DOCUMENTS

| | | |
|---|---|---|
| EP | 0558429 A1 | 9/1993 |
| EP | 0572131 A1 | 12/1993 |
| EP | 0648515 A1 | 4/1995 |
| EP | 0541930 B1 | 3/1998 |
| EP | 836868 A2 | 4/1998 |
| EP | 882955 A1 | 12/1998 |
| EP | 1278007 A1 | 1/2003 |
| EP | 1159926 A3 | 3/2003 |
| EP | 1810627 A1 | 7/2007 |
| EP | 2098184 A1 | 9/2009 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 2415630 A | 1/2006 |
| GB | 2434872 | 8/2007 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 2001003776 A | 1/2001 |
| JP | 200129356 | 2/2001 |
| JP | 200137775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 3618349 A2 | 6/1996 |
| WO | 3741924 A1 | 11/1997 |
| WO | 3743971 A2 | 11/1997 |
| WO | 3748449 A1 | 12/1997 |
| WO | 9748450 A1 | 12/1997 |
| WO | 9748451 A1 | 12/1997 |
| WO | 0036985 A2 | 6/2000 |
| WO | 0048672 A1 | 8/2000 |
| WO | 0049957 A1 | 8/2000 |
| WO | 0051513 A1 | 9/2000 |
| WO | 0057811 A1 | 10/2000 |
| WO | 0101847 A1 | 1/2001 |
| WO | 0174252 A2 | 10/2001 |
| WO | 0245790 A2 | 6/2002 |
| WO | 2002061880 A2 | 8/2002 |
| WO | 2004/112628 A1 | 12/2004 |
| WO | 2005011049 A2 | 2/2005 |
| WO | 2005016119 A2 | 2/2005 |
| WO | 2007024878 A1 | 3/2007 |
| WO | 2007076924 A2 | 7/2007 |
| WO | 2007112081 A1 | 10/2007 |
| WO | 2010035831 A1 | 4/2010 |

OTHER PUBLICATIONS

European Search Report EP 04752341.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
Search Report EP 05016399 dated Jan. 13, 2006.
Search Report EP 05017281 dated Nov. 24, 2005.
Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
Johnson et al., "Evaluation of a Bipolar Electrothermal Vessel Sealing Device in Hemontoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole MD. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N. J., 1970.
Kennedy et al., "High-burst-strength, feedback-controlled bipolar vessel sealing" Surgical Endoscopy (1998) 12: 376-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).

(56) References Cited

OTHER PUBLICATIONS

Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
European Search Report EP 06008779.8 dated Jul. 13, 2006.
Livraghi et al., (1995) "Saline-enhanced RF Tissue Ablation in the Treatment of Liver Metastases", Radiology, pp. 205-210.
Ni Wei et al., "A Signal Processing Method for the Coriolis Mass Flowmeter Based on a Normalized . . ." Journal of Applied Sciences Yingyong Kexue Xuebao, Shangha CN, vol. 23, No. 2:(Mar. 2005); pp. 160-184.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite Element Codes to Model Electrical Heating and Non Linear Thermal Transport in Biological Media", Proc. ASME HTD-355, 131 (1997).
Urologix, Inc.—Medical Professionals: Targis.TM. Technology (Date Unknown). "Overcoming the Challenge" located at: <(http://www.urologix.com/medicaUtechnology.html > last visited on Apr. 27, 2001, 3 pages.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, CarolinasMedicalCenter,Charlotte,NC 2003.
Cams et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndotHill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.

(56) References Cited

OTHER PUBLICATIONS

Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
ValleyLab Brochure, "Electosurgery: A Historical Overview", Innovations in Electrosurgery, 1999.
Vallfors et al., "Automatically Controlled Bipolar Electrocoagulation: 'COA-Comp'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 5/326,343, filed Jul. 1994, Rudie et al. (withdrawn).
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 05021780.1 dated Feb. 23, 2006.
Search Report EP 05021935 dated Jan. 27, 2006.
Search Report EP 05021936.9 dated Feb. 6, 2006.
Search Report EP 05021937.7 dated Jan. 23, 2006.
Search Report EP 05021939 dated Jan. 27, 2006.
Search Report EP 05021944.3 dated Jan. 25, 2006.
Search Report EP 05022350.2 dated Jan. 30, 2006.
Search Report EP 05023017.6 dated Feb. 24, 2006.
Search Report EP 05025421.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995): "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences.cndot. Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochennotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.

(56) References Cited

OTHER PUBLICATIONS

European Search Report EP 07009321.6 dated Aug. 28, 2007.
European Search Report EP 07009322.4 dated Jan. 14, 2008.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Intl Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal DT Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 110-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: http://www.urologix.com/medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
Carus et al., "Initial Experience With the LigaSure.TM. Vessel Sealing System in Abdominal Surgery" Innovations That Work, Jun. 2002.
Cosman et al., "Methods of Making Nervous System Lesions" in William RH, Rengachary SS (eds): Neurosurgery, New York: McGraw-Hill, vol. 111, (1984), pp. 2490-2499.
Esterline, "Light Key Projection Keyboard" 2004 Advanced Input Systems, located at: <http://www.advanced-input.com/lightkey> last visited on Feb. 10, 2005.
Herman et al., "Laparoscopic Intestinal Resection With the LigaSure.TM. Vessel Sealing System: A Case Report" Innovations That Work, Feb. 2002.

* cited by examiner

MICROWAVE ANTENNA WITH COOLED HANDLE

CROSS REFERENCE TO RELATED APPLICATIONS

This application is a continuation application of U.S. patent application Ser. No. 15/194,810, filed on Jun. 28, 2016, now U.S. Pat. No. 9,707,038, which is a continuation application of U.S. patent application Ser. No. 14/925,025, filed on Oct. 28, 2015, now U.S. Pat. No. 9,375,280, which is a continuation application of U.S. patent application Ser. No. 14/659,860, filed on Mar. 17, 2015, now U.S. Pat. No. 9,198,725, which is a continuation application of U.S. patent application Ser. No. 14/338,509, filed Jul. 23, 2014, now U.S. Pat. No. 9,113,932, which is a continuation application of U.S. patent application Ser. No. 14/014,937, filed Aug. 30, 2013, now U.S. Pat. No. 8,795,268, which is a continuation application of U.S. patent application Ser. No. 13/596,785, filed Aug. 28, 2012, now U.S. Pat. No. 8,523,854, which is a continuation application of U.S. patent application Ser. No. 12/199,935, filed Aug. 28, 2008, now U.S. Pat. No. 8,251,987, the entire contents each of which are incorporated herein by reference.

BACKGROUND

1. Technical Field

The present disclosure relates generally to microwave antennas used in tissue ablation procedures. More particularly, the present disclosure is directed to a microwave antenna having a coolant assembly for circulating a dielectric coolant fluid through the microwave antenna.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Conventional microwave antennas have a narrow operational bandwidth, a wavelength range at which optimal operational efficiency is achieved, and hence, are incapable of maintaining a predetermined impedance match between the microwave delivery system (e.g., generator, cable, etc.) and the tissue surrounding the microwave antenna. More specifically, as microwave energy is applied to tissue, the dielectric constant of the tissue immediately surrounding the microwave antenna decreases as the tissue is cooked. The drop causes the wavelength of the microwave energy being applied to tissue to increase beyond the bandwidth of the antenna. As a result, there is a mismatch between the bandwidth of conventional microwave antenna and the microwave energy being applied. Thus, narrow band microwave antennas may detune hindering effective energy delivery and dispersion.

SUMMARY

According to one aspect of the present disclosure, a microwave antenna assembly is disclosed. The antenna assembly includes a feedline having an inner conductor, an outer conductor and an inner insulator disposed therebetween and a radiating portion including a dipole antenna having a proximal portion and a distal portion. The antenna assembly also comprises a sheath disposed over the feedline and the radiating portion defining a chamber around the feedline and the radiating portion. The chamber is adapted to circulate coolant fluid therethrough. The antenna assembly further includes a connection hub having cable connector coupled to the feedline, an inlet fluid port and an outlet fluid port. The connection hub includes a bypass tube configured to provide for flow of the coolant fluid from the cable connector directly to the outlet fluid port.

According another aspect of the present disclosure, a microwave antenna assembly is disclosed. The antenna assembly includes a feedline having an inner conductor, an outer conductor and an inner insulator disposed therebetween and a radiating portion including a dipole antenna having a proximal portion and a distal portion. The antenna assembly also comprises a sheath disposed over the feedline and the radiating portion defining a chamber around the feedline and the radiating portion. The chamber is adapted to circulate coolant fluid therethrough. The antenna assembly further includes a three-branch connection hub including a first branch having a cable connector coupled to the feedline at a junction point, a second branch having an outlet port, a third branch having an inlet port, and a bypass tube in fluid communication with a proximal end of the first branch and the outlet port, wherein one end of the bypass tube is in proximity with the junction point to provide for flow of the coolant fluid therethrough.

A method for manufacturing a microwave antenna assembly is also contemplated by the present disclosure. The antenna assembly includes a feedline including an inner conductor, an outer conductor and an inner insulator disposed therebetween and a radiating portion including a dipole antenna having a proximal portion and a distal portion. The method includes the step of enclosing the feedline and the radiating portion in a sheath to define a chamber around the feedline and the radiating portion. The chamber is adapted to circulate coolant fluid therethrough. The method also includes the step of coupling a three-branch connection hub to the feedline and the sheath. The three-branch connection hub including a first branch having a cable connector coupled to the feedline at a junction point, a second branch having an outlet port, a third branch having an inlet port. A step of interconnecting a proximal end of the first branch and the outlet port via a bypass tube is also provided by the method. One end of the bypass tube is in proximity with the junction point to provide for flow of the coolant fluid therethrough.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
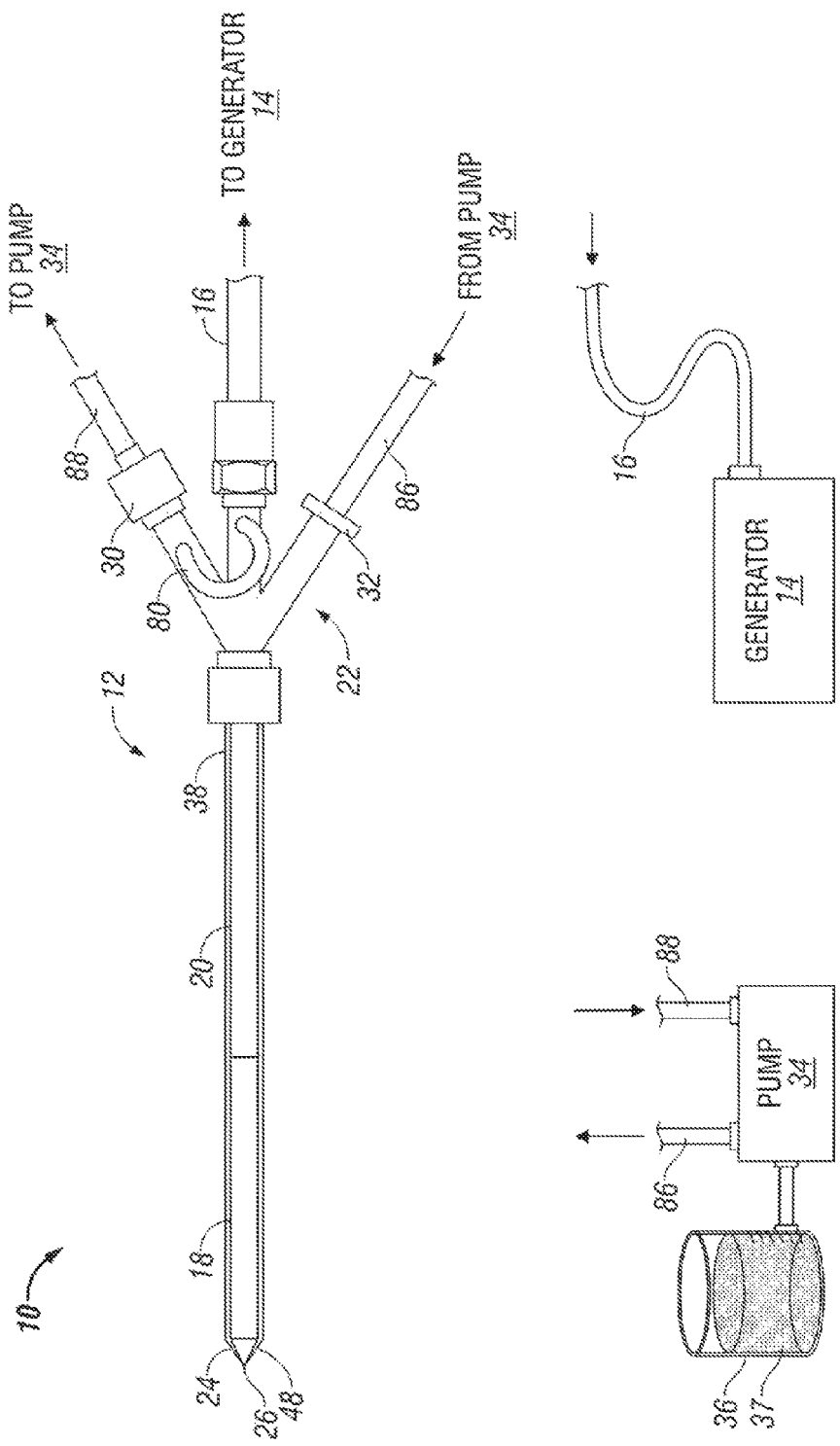
FIG. 1 is a schematic diagram of the microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 5000 MHz although other suitable frequencies are also contemplated.

The antenna assembly 12 includes a radiating portion 18 connected by feedline 20 (or shaft) to the cable 16. More specifically, the antenna assembly 12 is coupled to the cable 16 through a connection hub 22 having an outlet fluid port 30 and an inlet fluid port 32 that are connected in fluid communication with a sheath 38. The sheath 38 encloses radiating portion 18 and feedline 20 allowing a coolant fluid 37 to circulate from ports 30 and 32 around the antenna assembly 12. The ports 30 and 32 are also coupled to a supply pump 34 that is, in turn, coupled to a supply tank 36 via supply line 86. The supply pump 34 may be a peristaltic pump or any other suitable type. The supply tank 36 stores the coolant fluid 37 and in one embodiment, may maintain the fluid at a predetermined temperature. More specifically, the supply tank 36 may include a coolant unit that cools the returning liquid from the antenna assembly 12. In another embodiment, the coolant fluid 37 may be a gas and/or a mixture of fluid and gas.

Figure 2:
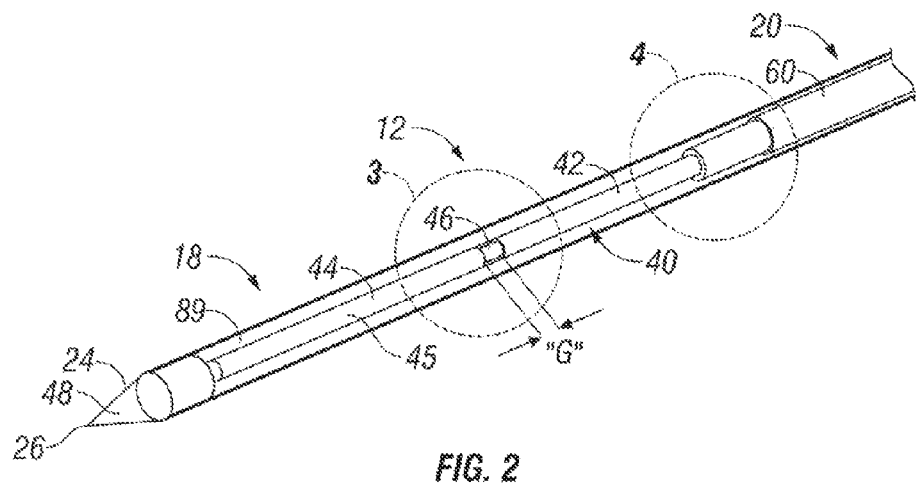
FIG. 2 is a perspective, internal view of the microwave antenna assembly according to the present disclosure.
Figure 3:
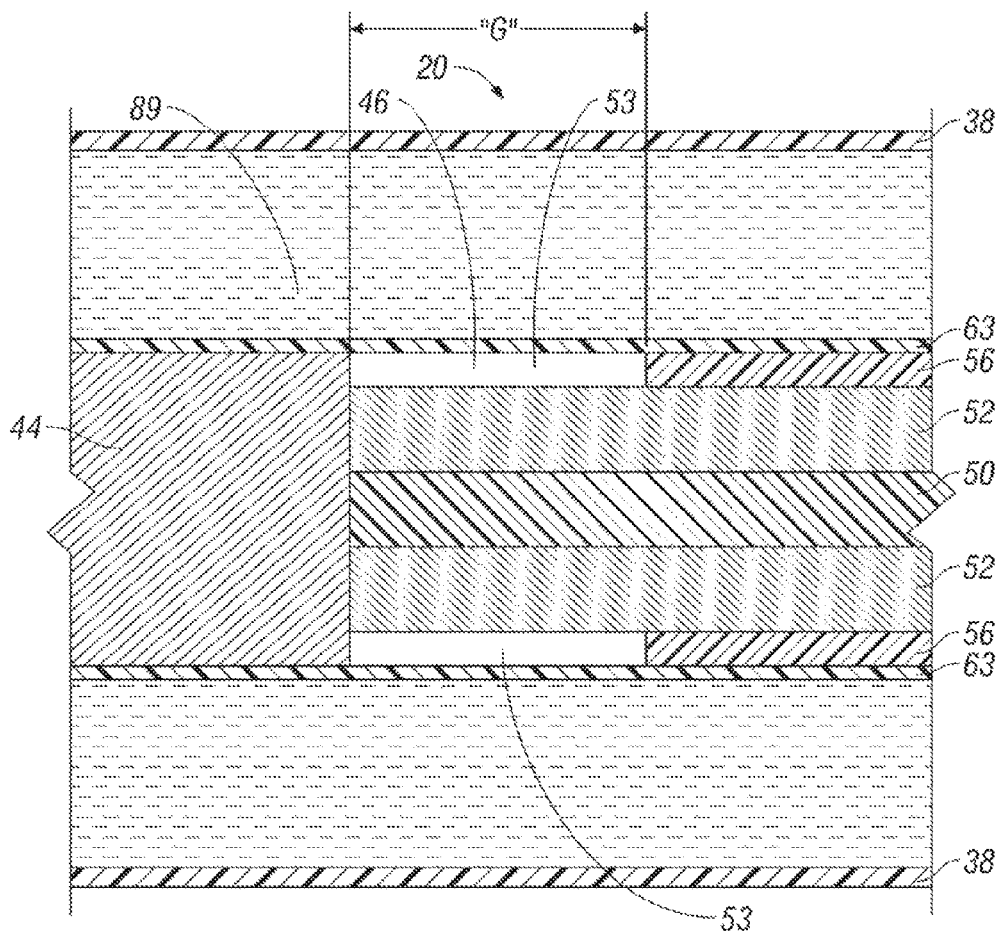
FIGS. 3 and 4 are enlarged, cross-sectional views of a portion of the microwave antenna assembly of FIG. 1.
Figure 4:
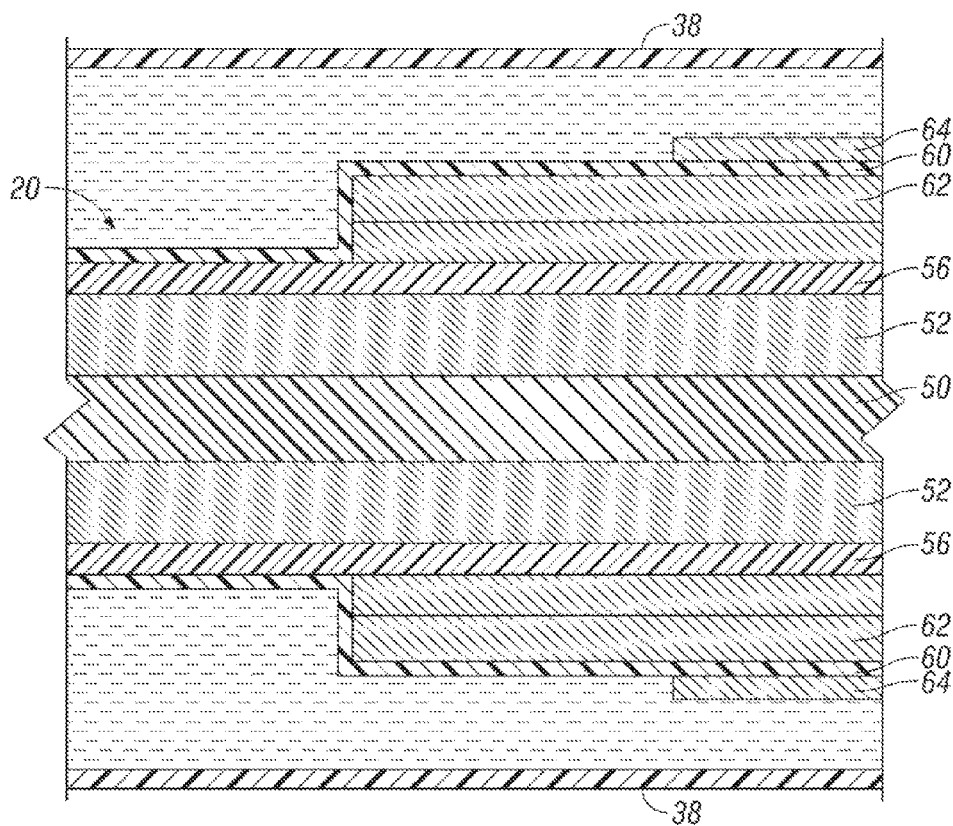

FIG. 2 illustrates the radiating portion 18 of the antenna assembly 12 having a dipole antenna 40. The dipole antenna 40 is coupled to the feedline 20 that electrically connects antenna assembly 12 to the generator 14. As shown in FIG. 3-4, the feedline 20 includes an inner conductor 50 (e.g., wire) surrounded by an inner insulator 52, which is surrounded by an outer conductor 56 (e.g., cylindrical conducting sheath). The inner and outer conductors 50 and 56 respectively, may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial semi-rigid or flexible cable having a wire with a 0.047" outer diameter rated for 50 Ohms.

The dipole antenna 40 includes a proximal portion 42 and a distal portion 44 interconnected at a feed point 46. The distal portion 44 and the proximal portion 42 may be either balanced (e.g., of equal lengths) or unbalanced (e.g., of unequal lengths). The proximal portion 42 is formed from the inner conductor 50 and the inner insulator 52 which are extended outside the outer conductor 56, as shown best in FIG. 4. In one embodiment, in which the feedline 20 is formed from a coaxial cable, the outer conductor 56 and the inner insulator 52 may be stripped to reveal the inner conductor 50, as shown in FIG. 3.

FIG. 3 illustrates the distal portion 44 attached to the proximal portion 42. The distal portion 44 may be soldered to the inner conductor 50 of the proximal portion 42 to establish electromechanical contact therebetween. A portion of the distal end of the inner conductor 50 is inserted into the distal portion 44 such that a dipole feed gap "G" remains between the proximal and distal portions 42 and 44 at the feed point 46. The gap "G" may be from about 1 mm to about 3 mm. In one embodiment, the gap "G" may be thereafter filled with a dielectric material at the feed point 46. In another embodiment, the inner insulator 52 is extended into the feed point 46. The dielectric material may be polytetrafluoroethylene (PTFE), such as Teflon® sold by DuPont of Willmington, Del. In another embodiment, as shown in FIG. 3, the gap "G" may be coated with a dielectric seal coating as discussed in more detail below.

With reference to FIGS. 2 and 4, the antenna assembly 12 also includes a choke 60. The choke 60 is disposed around the feedline 20 and includes an inner dielectric layer 62 and an outer conductive layer 64. The choke 60 may be a quarter-wavelength shorted choke and is shorted to the outer conductor 56 of the feedline 20 at the proximal end (not illustrated) of the choke 60 by soldering or other suitable methods. In one embodiment, the dielectric layer 62 is formed from a fluoropolymer, such as tetrafluoroethylene, perfluorpropylene, and the like, and has a thickness of about 0.005 inches. The dielectric of dielectric layer 62 may extend past the choke conductor layer 64 toward the distal end of the assembly 12, as shown in FIG. 2.

Since the radiating portion 18 and the feedline 20 are in direct contact with the coolant fluid 37 these components of the assembly 12 are sealed by a protective sleeve 63 (FIG. 3) to prevent any fluid seeping therein. This may be accomplished by applying any type of melt-processable polymers using conventional injection molding and screw extrusion techniques. In one embodiment, a sleeve of fluorinated ethylene propylene (FEP) shrink wrap may be applied to the entire assembly 12, namely the feedline 20 and the radiating portion 18, as shown in FIGS. 3 and 4. The protective sleeve 63 is then heated to seal the feedline 20 and radiating portion 18. The protective sleeve 63 prevents any coolant fluid 37 from penetrating into the assembly 12. The protective sleeve 63 may be applied either prior to or after applying the outer conductive layer 64. In addition, protective sleeve 63 may also be applied at the point where the inner conductor 50 and the inner insulator 52 are extended past the outer conductor 56, thereby creating a vacuum 53 as shown in FIG. 3.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat.

The tip 48, which may be formed from a variety of heat-resistant materials suitable for penetrating tissue, such as metals (e.g., stainless steel) and various thermoplastic materials, such as poletherimide, polyamide thermoplastic resins, an example of which is ULTEM® resin sold by General Electric Co. of Fairfield, Conn. The tip 48 may be machined from various stock rods to obtain a desired shape. The tip 48 may be attached to the distal portion 44 using various adhesives, such as epoxy seal. If the tip 48 is metal, the tip 48 may be soldered to the distal portion 44.

Figure 5:
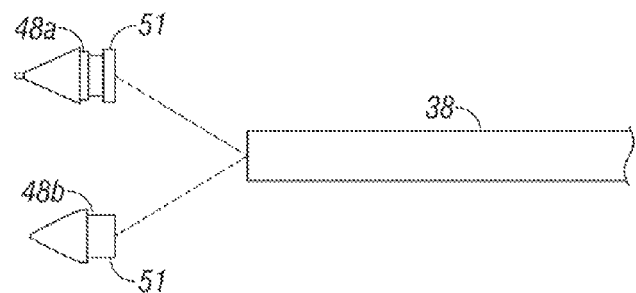
FIG. 5 is a side view of an interchangeable tip (or a sheath and a tip assembly) for use with the microwave antenna assembly of FIG. 1.
Figure 6:
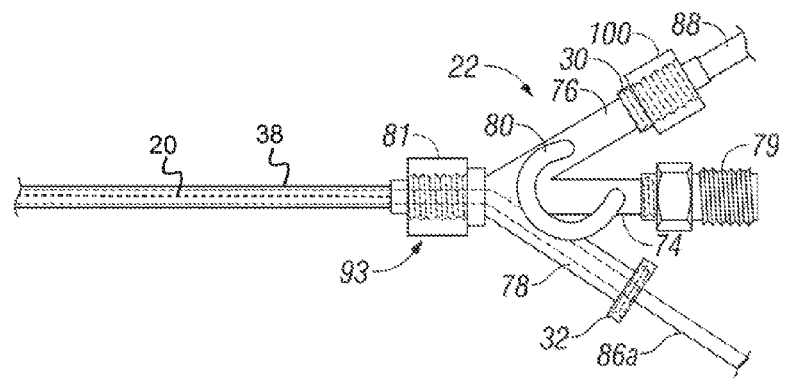
FIG. 6 is a schematic, top view of a connection hub of the microwave antenna assembly of FIG. 1 according to the present disclosure.

FIG. 5 illustrates various shapes and forms of the tip 48, namely a stainless steel tip 48a and a dielectric tip 48b. Both tips 48a and 48b include an insertion base 51 having an external diameter that is smaller than diameter of the tips 48a and 48b allowing for easier insertion into the sheath 38. This configuration also provides for a better seal between the tip 48 and the sheath 38. The sheath 38 encloses the feedline 20, the radiating portion 18 from the tip 48 to the base 81 (FIG. 6). The sheath 38 is also secured to the base 81 of the connection hub 22 and the tip 48 such that the sheath 38 is in fluid communication with the connection hub 22 and defines a chamber 89 (FIG. 3) between the base 81 and the tip 48. The coolant fluid 37 is supplied by the pump 34 and is circulated in the chamber 89 between the radiating portion 18, the feedline 20 and the sheath 38. The sheath 38 may be any type of rigid tube, such as a catheter manufactured from polyimide and other types of polymers. The sheath 38 may be assembled by initially securing the tip 48 to the distal end of the sheath 38 and then inserting the combined sheath and tip assembly onto the assembly 12.

The assembly 12 also includes the connection hub 22, as shown in more detail in FIG. 6. The connection hub 22 includes a cable connector 79 and fluid ports 30 and 32. The connection hub 22 may include a three-branch luer type connector 72, with a first branch 74 being used to house the cable connector 79 and the second and third branches 76 and 78 to house the outlet and inlet fluid ports 30 and 32, respectively. In one embodiment, the connection hub 22 may include only the first branch 74 or two of the branches 74, 76, 78 and have the fluid ports 30 and 32 disposed directly on the first branch 74.

The connection hub 22 also includes a base 81 disposed at a distal end of the first branch 74. More than one inflow 86 and outflow 88 tube may be used. The outflow tube 88 is coupled to the second branch 76 and is in fluid communication with the bypass tube 80 through the second branch 76. In one embodiment, the assembly 12 includes one or more inflow tubes 86a and 86b that are fed through the third branch 78 as shown in FIG. 6.

Figure 7:
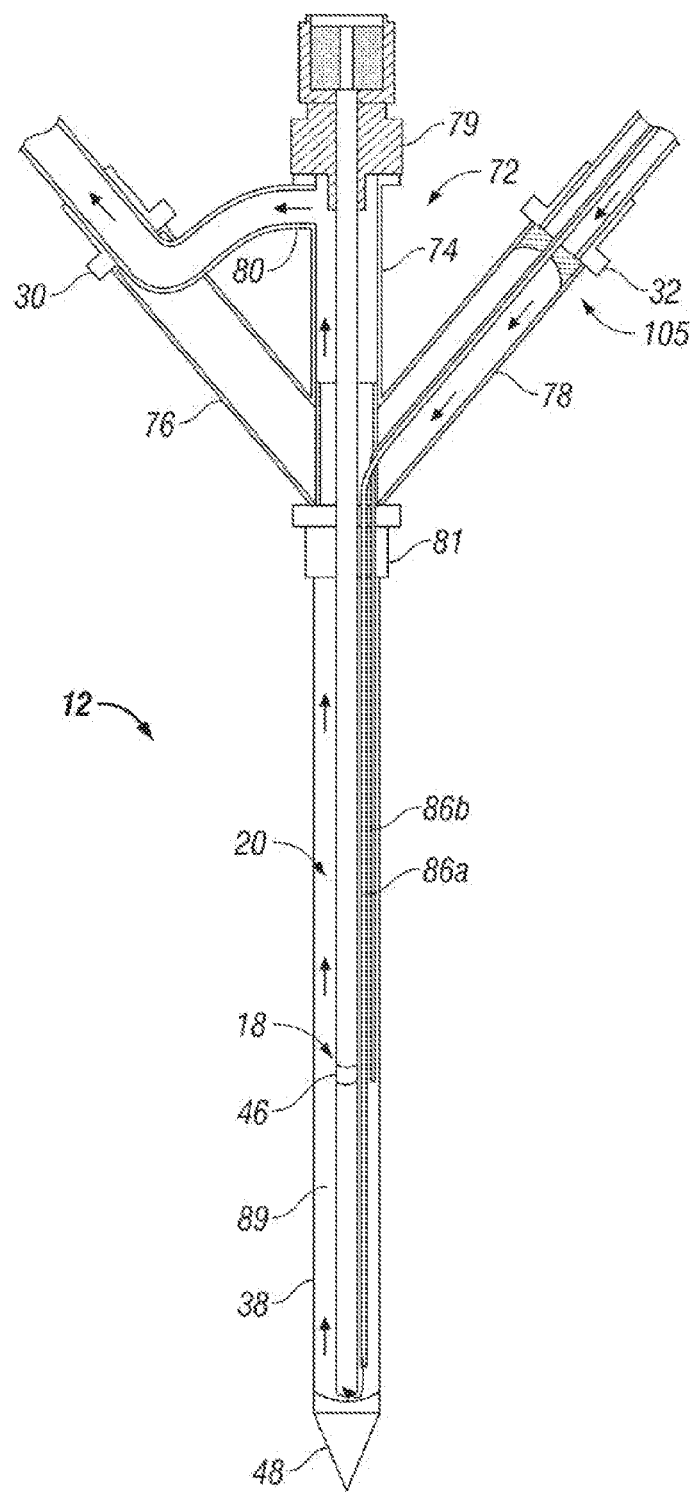
FIG. 7 a cross-sectional view of a series of inflow tubes of the microwave antenna assembly of FIG. 1 according to the present disclosure.
Figure 8:
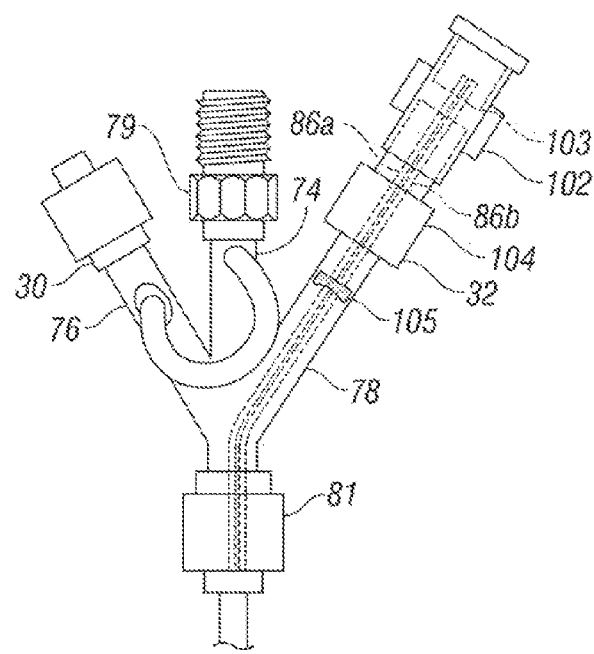
FIG. 8 is a topside view of a proximal portion of the microwave antenna assembly of FIG. 1 according to the present disclosure.

In one embodiment, the second and third branches 76 and 78 may include various types of female and/or male luer connectors adapted to couple inflow and outflow tubes 86 and 88, respectively, from the pump 34 to the assembly 12. FIG. 7 shows the assembly 12 including two inflow tubes 86a and 86b. The inflow tubes 86a and 86b may be any type of flexible tube having an external diameter sufficient to fit inside a chamber 89 between the feedline 20 and the sheath 38. The inflow tubes 86a and 86b are inserted through the inlet fluid port 32. More specifically, as illustrated in FIG. 8, a female connector 102 may be coupled to the inlet port 32 either directly or to an intermediate male luer connector 104. The distal ends of the tubes 86a and 86b are inserted through an internal support member 103 of the female connector 102, which secures the tubes 86a and 86b thereto. The female and male connectors 102 and 104 allow for easy coupling of the assembly 12 to the coolant fluid system. The inflow tubes 86a and 86b may be secured to the third branch 78 via a glue plug 105, which may be formed by flowing glue into the third branch 78 and curing the glue via an ultraviolet source or other way known in the art.

The inflow tube 86a is inserted into the distal end of the distal portion 44 and the inflow tube 86b is inserted at a point proximate the midpoint of the assembly 12 (e.g., the feed point 46), as shown in FIG. 7. The inflow tubes 86a and 86b are then secured to the radiating portion 18 (e.g., using epoxy, glue, etc.). The inflow tubes 86a and 86b are positioned in this configuration to provide optimal coolant flow through the sheath 38. The fluid flow from the inflow tube 86a is directed into the tip 48 and reflected in the proximal direction. The fluid flow from the inflow tube 86b provides the coolant fluid 37 along the radiating portion 18. During operation, the pump 34 supplies fluid to the assembly 12 through the inflow tubes 86a and 86b, thereby circulating the coolant fluid 37 through the entire length of the assembly 12 including the connection hub 22. The coolant fluid 37 is then withdrawn from the first branch 74 and the second branch 76 through the outlet fluid port 30.

The above-discussed coolant system provides for circulation of dielectric coolant fluid 37 (e.g., saline, deionized water, etc.) through the entire length of the antenna assembly 12. The dielectric coolant fluid 37 removes the heat generated by the assembly 12. In addition, the dielectric coolant fluid 37 acts as a buffer for the assembly 12 and prevents near field dielectric properties of the assembly 12 from changing due to varying tissue dielectric properties. For example, as microwave energy is applied during ablation, desiccation of the tissue around the radiating portion 18 results in a drop in tissue complex permittivity by a considerable factor (e.g., about 10 times). The dielectric constant (er') drop increases the wavelength of microwave energy in the tissue, which affects the impedance of unbuffered microwave antenna assemblies, thereby mismatching the antenna assemblies from the system impedance (e.g., impedance of the cable 16 and the generator 14). The increase in wavelength also results in a power dissipation zone which is much longer in length along the assembly 12 than in cross sectional diameter. The decrease in tissue conductivity (er") also affects the real part of the impedance of the assembly 12. The fluid dielectric buffering according to the present disclosure also moderates the increase in wavelength of the delivered energy and drop in conductivity of the near field, thereby reducing the change in impedance of the assembly 12, allowing for a more consistent antenna-to-system impedance match and spherical power dissipation zone despite tissue behavior.

Figure 9:
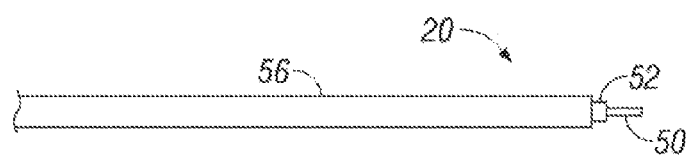
FIG. 9 is a side view of a proximal end of the feedline of the microwave antenna assembly of FIG. 1 according to the present disclosure.
Figure 10:
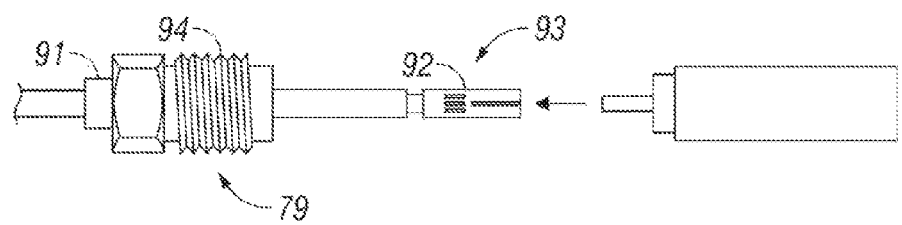
FIG. 10 is a side view of a cable connector of the microwave antenna assembly of FIG. 1 according to the present disclosure.

Referring to FIGS. 9 and 10, the cable connector 79 is coupled to the inner conductor 50 and outer conductor 56. More specifically, the inner conductor 50 and the inner insulator 52 extend outside the outer conductor 56 at the proximal end of the feedline 20 and the cable connector 79 is coupled to the inner and outer conductors 50 and 56. The cable connector 79 may be any type of threaded or snap connector adapted to contact the outer conductor 56 and the inner conductor 50. In one embodiment, the cable connector 79 may be an SMA type connector having an outer conductor 91, an insulator (not explicitly shown), and an inner conductor 92, which may be a hollow pin. The inner conductor 92 of the cable connector 79 fits about the inner conductor 50 and the outer conductor 91 thereof contacts the outer conductor 56, with the insulator spacing the outer and inner conductors 91 and 92 apart. Cable connector 79 may be secured to the inner and outer conductors 50 and 56 using soldering, laser welding and other suitable ways, which provide electromechanical contact therebetween at a junction point 93.

Laser welding allows coupling the cable connector 79 to the feedline 20. However, care must be exercised to avoid damaging the outer conductor 56 by the laser. Soldering avoids this issue, but at higher power levels (e.g., about 90 or more Watts) the soldering connection may begin to reflow due to the excessive heat generated by increased power. Embodiments of the present disclosure also provide for a system and method to alleviate the solder reflow by circulating a dielectric coolant fluid through the entire length of the assembly 12 up to the cable connector 79 such that the junction point 93 of the connector 79 to the inner and outer conductors 50 and 56 is cooled.

The connector 79 includes a threaded portion 94 that couples to the distal end of the cable 16, which may also have a corresponding SMA male connector. The connection hub 22 is inserted onto the distal end of the feedline 20 and is slid toward the distal end thereof. The cable connector 79 is then coupled to the proximal end of the first branch 74 thereby securing the connector hub 22 to the feedline 20 (e.g., gluing the connector hub 22 to the cable connector 79).

Figure 11:
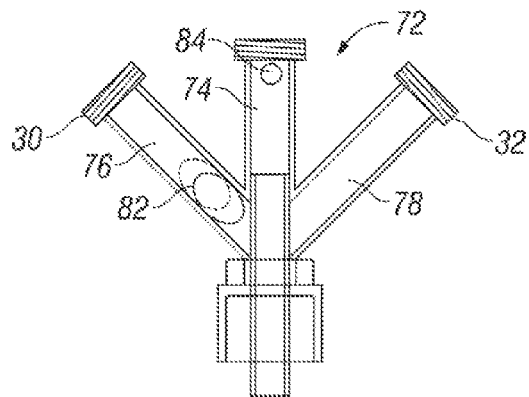
FIG. 11 is a top view of a connection hub of the microwave antenna assembly of FIG. 1 according to the present disclosure.
Figure 12A:
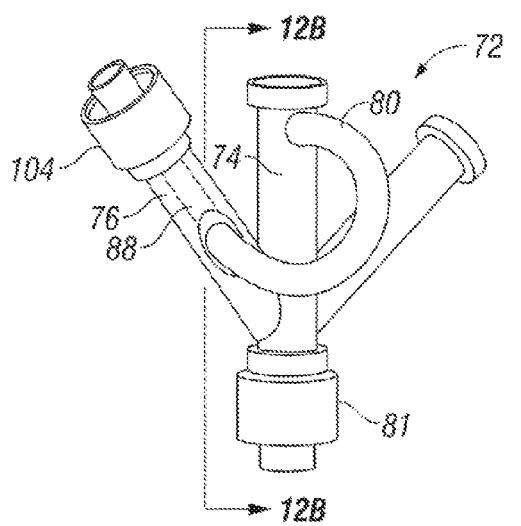
FIGS. 12A and B are perspective and side views of the connection hub of the microwave antenna assembly of FIG. 1 according to the present disclosure.
Figure 12B:
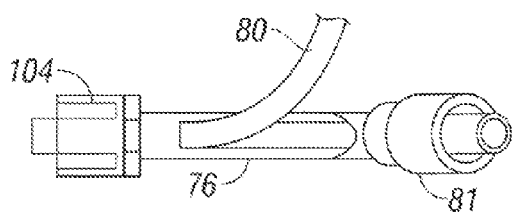
Figure 13:
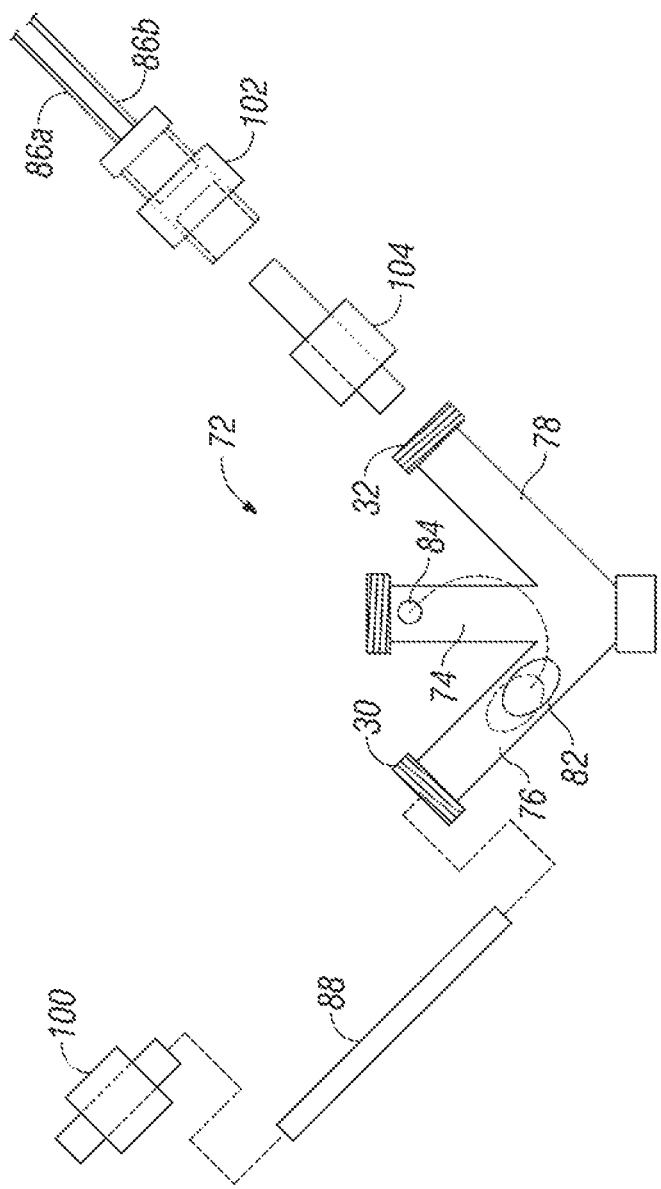
FIG. 13 is a top view of a connection hub of the microwave antenna assembly of FIG. 1 with parts disassembled according to the present disclosure.

FIGS. 11 and 12 illustrate one embodiment wherein the first and second branches 74 and 76 are interconnected via a bypass tube 80. A beveled opening 82 is formed in the wall of the second branch 76 and is angled toward the outlet fluid port 30, as shown in FIG. 11. This configuration provides easier insertion of the bypass tube 80 into the second branch 76 as shown in FIGS. 12A-B and 13. An outlet opening 84 is also formed in the first branch 74, at approximately the proximal end thereof such that the outlet opening 84 is proximate the junction point 93 of the connector 79 and the feedline 20 allowing the coolant fluid 37 to contact the connector 79. The outlet opening 84 may be formed at any angle suitable for providing fluid flow between the first branch 74 and the second branch 76. A first end of the bypass tube 80 is attached to the outlet opening 84 such that the first end of the bypass tube 80 is proximate to the junction point 93. A second end of the bypass tube 80 is thereafter inserted through the second branch 76 and the outlet port 30 and is coupled to a male luer type connector 100, which provides for quick coupling and decoupling to the outflow tube 88, as shown in FIG. 13. The bypass tube 80 may be attached to the openings 82 and 84 using a variety of adhesives and other means suitable for sealing any gaps between the openings 82 and 84 and the bypass tube 80. The bypass tube 80 may be compression fit into the male connector 100 and/or glued thereto. The outlet port 30 is sealed via a glue plug or other means around the bypass tube 80, thereby limiting the coolant fluid 37 to outflow through the bypass tube 80. This configuration allows the coolant fluid to flow from the assembly 12 only through the opening 84.

In conventional designs, vapor pockets form at the junction between the connector 79 and the feedline 20 and prevent the coolant fluid 37 from reaching the connector 79, thereby preventing any cooling to take place. As a result, the connector 79 continues to heat up and solder attaching the coupling the connector 79 melts. The bypass tube 80 provides for unrestricted flow of the coolant fluid from the proximal end of the first branch 74 and the connector 79. The bypass tube 80 provides for flow of the coolant fluid directly from the cable connector 79 to the outlet port 30 without withdrawing fluid through the second branch 76. This configuration removes the fluid from the assembly 12 at a rate sufficient to prevent vaporization of the fluid as it comes in contact with the junction point 93 of the connector 79, thereby preventing formation of vapor pockets. In other words, the bypass tube 80 allows for the coolant fluid to circuit to the connector 79 without restrictions caused by pressure build-up resulting from the heat generated at the junction point 93.

The above-discussed coolant system provides circulation of dielectric coolant fluid 37 (e.g., saline, deionized water, etc.) through the entire length of the antenna assembly 12. In addition, the coolant is also brought in contact with the cable connector 79 allowing use of a conventional solder connection to attach the connector 79 to the feedline 20. The fluid provides cooling and enhances dielectric matching properties of the assembly 12. The coolant fluid 37 supplied to the cable connector 79 prevents solder re-flow, allowing the assembly 12 to operate at higher power levels (e.g., 150 watts). The coolant fluid 37 circulated through the sheath 38 also wicks heat away from the feedline 20, which allows delivery of high power signals to the antenna radiating section.

Figure 14:
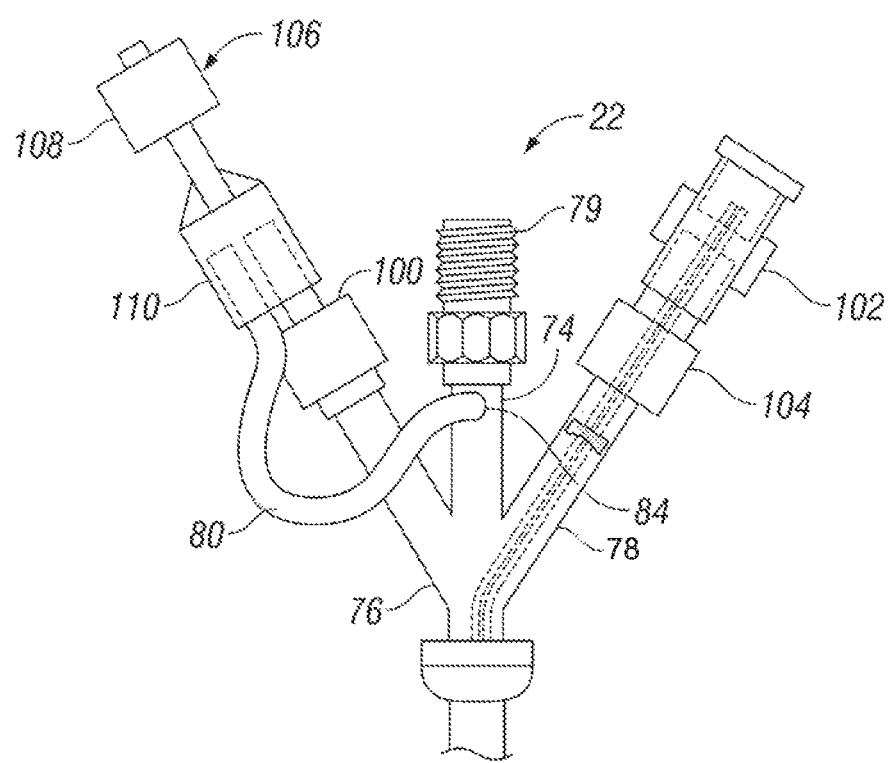
FIG. 14 is a top view of a connection hub of the microwave antenna assembly of FIG. 1 according to one embodiment of the present disclosure.
Figure 15:
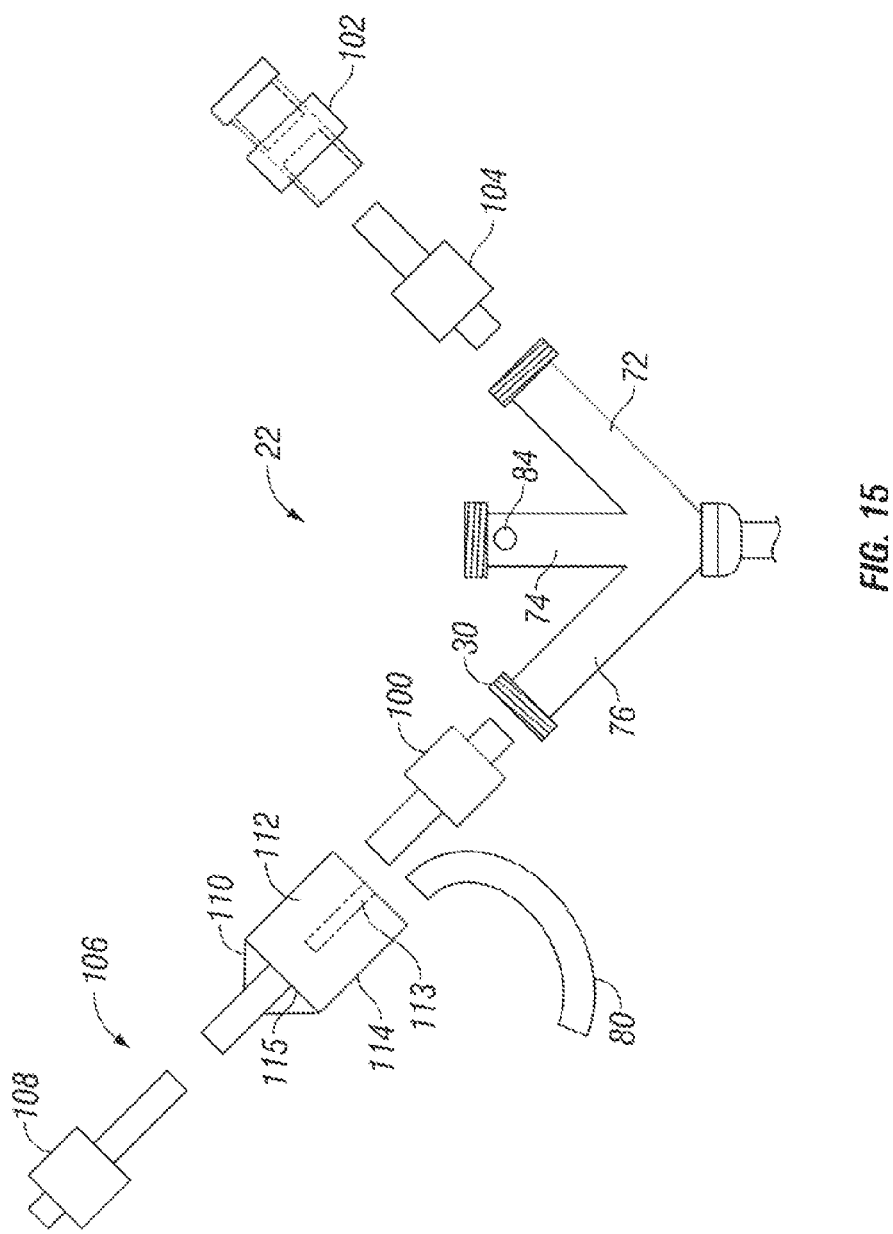
FIG. 15 is a top view of a connection hub of the microwave antenna assembly of FIG. 1 with parts disassembled according to one embodiment of the present disclosure.

FIGS. 14 and 15 illustrate another embodiment of the connection hub 22 having a bifurcated outflow path configuration, in which the second branch 76 also acts as an outflow path. The connection hub 22 as shown in FIG. 14 does not include the beveled opening 82 since the bypass tube 80 is coupled to the opening 84 within the first branch 74 and is fed directly into a bifurcated coupler 106. The bifurcated coupler 106 includes a male luer connector 108 at a proximal end thereof and a bifurcated port 110 at a distal end thereof. The bifurcated port 110 includes a first port 112 and a second port 114 which are separated by a member 113 at the distal end of the bifurcated port 110 such that the first and second ports 112 and 114 then meet at a chamber 115. The first port 112 is coupled to the second branch 76 through the connector 100 and the second port 114 is coupled to bypass tube 80. This configuration provides for a dual outflow of the coolant fluid 37, from the second branch 76 and the bypass tube 80 and allows for an increased flow rate through the assembly 12.

The described embodiments of the present disclosure are intended to be illustrative rather than restrictive, and are not intended to represent every embodiment of the present disclosure. Embodiments of the present disclosure may also be implemented in a microwave monopolar antenna or other electrosurgical devices. Various modifications and variations can be made without departing from the spirit or scope of the disclosure as set forth in the following claims both literally and in equivalents recognized in law.

What is claimed is:

1. An electrosurgical energy delivery device comprising:
    a hub including a proximal portion and a distal portion;
    a sheath extending distally from the hub, the sheath defining a chamber;
    a feedline configured to deliver electrosurgical energy, the feedline including an inner conductor, an outer conductor, and an inner insulator disposed between at least a portion of the inner conductor and the outer conductor, wherein at least a portion of the feedline is disposed within the chamber defined by the sheath; and
    a fluid flow tube disposed within the chamber defined by the sheath, the fluid flow tube configured to deliver a fluid to the chamber defined by the sheath to cool the portion of the feedline disposed within the chamber defined by the sheath and to return the fluid to the hub.

2. The electrosurgical energy delivery device according to claim 1, wherein the fluid is a gas, a liquid, or a combination of a gas and a liquid.

3. The electrosurgical energy delivery device according to claim 1, further comprising:
    a dielectric layer formed circumferentially about at least a portion of the outer conductor; and
    a conductive layer formed circumferentially about at least a portion of the dielectric layer, at least a portion of the conductive layer electrically coupled to a portion of the outer conductor of the feedline, wherein the dielectric layer and the conductive layer limit propagation of electrosurgical energy in a proximal direction.

4. The electrosurgical energy delivery device according to claim 3, wherein the conductive layer includes a proximal portion electrically coupled to the outer conductor of the feedline.

5. The electrosurgical energy delivery device according to claim 3, wherein the dielectric layer and the conductive layer define a quarter wavelength choke.

6. The electrosurgical energy delivery device according to claim 3, further comprising a second dielectric layer formed circumferentially about the dielectric layer between the dielectric layer and the conductive layer.

7. The electrosurgical energy delivery device according to claim 3, wherein the feedline includes a radiating portion configured to deliver microwave energy to tissue and a distal portion of the conductive layer is disposed proximal a proximal portion of the radiating portion.

8. The electrosurgical energy delivery device according to claim 1, wherein the fluid flow tube extends through the hub and into the chamber defined by the sheath.

9. The electrosurgical energy delivery device according to claim 1, wherein the fluid flow tube is disposed adjacent at least a portion of the feedline within the chamber defined by the sheath.

10. The electrosurgical energy delivery device according to claim 1, wherein the feedline includes a radiating portion configured to deliver microwave energy to tissue and wherein a distal portion of the fluid flow tube is disposed proximal to the radiating portion.

11. The electrosurgical energy delivery device according to claim 1, wherein fluid flow from the fluid flow tube is directed in a direction of a tip disposed at a distal portion of the electrosurgical energy delivery device and reflected in a proximal direction.

12. The electrosurgical energy delivery device according to claim 1, further comprising a second fluid flow tube configured to deliver fluid, a distal portion of the second flow tube disposed distal a distal portion of the fluid flow tube.

13. A system comprising:
    an electrosurgical energy generator;
    a fluid supply; and
    an electrosurgical energy delivery device configured to couple to the electrosurgical energy generator and the fluid supply, the electrosurgical energy delivery device comprising:
        a hub including a proximal portion and a distal portion;
        a sheath extending distally from the hub, the sheath defining a chamber;
        a feedline configured to deliver microwave energy generated by the microwave generator, the feedline including an inner conductor, an outer conductor, and an inner insulator disposed between at least a portion of the inner conductor and the outer conductor, wherein at least a portion of the feedline is disposed within the chamber defined by the sheath; and
        a fluid flow tube disposed within the chamber defined by the sheath, the fluid flow tube configured to deliver a fluid from the fluid supply to the chamber defined by the sheath to cool the portion of the feedline disposed within the chamber defined by the sheath and to return the fluid to the hub.

14. The system according to claim 13, wherein the fluid is a gas, a liquid or a combination of a gas and a liquid.

15. The system according to claim 13, wherein the electrosurgical energy delivery device includes:
    a dielectric layer formed circumferentially about at least a portion of the outer conductor; and
    a conductive layer formed circumferentially about at least a portion of the dielectric layer, at least a portion of the conductive layer electrically coupled to a portion of the outer conductor of the feedline, wherein the dielectric layer and the conductive layer limit propagation of electrosurgical energy in a proximal direction.

16. The system according to claim 15, wherein the conductive layer includes a proximal portion electrically coupled to the outer conductor of the feedline.

17. The system according to claim 15, wherein the dielectric layer and the conductive layer define a quarter wavelength choke.

18. The system according to claim 15, wherein the electrosurgical energy delivery device includes a second dielectric layer formed circumferentially about the dielectric layer between the dielectric layer and the conductive layer.

19. The system according to claim 13, wherein the feedline includes a radiating portion configured to deliver microwave energy to tissue and a distal portion of the conductive layer is disposed proximal a proximal portion of the radiating portion.

20. The system according to claim 13, wherein the electrosurgical energy delivery device includes a second fluid flow tube configured to deliver fluid, a distal portion of the second flow tube disposed distal a distal portion of the fluid flow tube.

* * * * *